United States Patent [19]

Demarchez et al.

[11] Patent Number: 6,004,987

[45] Date of Patent: *Dec. 21, 1999

[54] USE OF LIGANDS WHICH ARE SPECIFIC FOR RXR RECEPTORS

[75] Inventors: Michel Demarchez, Le Bar sur Loup; André Jomard, Saint Vallier de Thiey, both of France

[73] Assignee: Centre International de Recherches Dermatologiques Galderma, Valbonne, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/666,799

[22] Filed: Jun. 19, 1996

[30] Foreign Application Priority Data

Jun. 19, 1995 [FR] France ................................ 95 07300

[51] Int. Cl.[6] ........................ A61K 31/455; A61K 31/38; A61K 31/20; A61K 31/59
[52] U.S. Cl. ......................... 514/356; 514/443; 514/448; 514/559; 514/560; 514/563; 514/568; 514/569; 514/729
[58] Field of Search ....................... 514/448, 443, 514/559, 560, 563, 568, 569, 729, 356

[56] References Cited

FOREIGN PATENT DOCUMENTS

94/15901  7/1994  WIPO .
94/17796  8/1994  WIPO .

OTHER PUBLICATIONS

Mol. Cell. Biol., vol. 15, No. 12, 1995, pp. 6481–6487.

J. Biol. Chem., vol. 267, No. 31, 1992, pp. 22010–22013.

Hashimoto Y et al. Biochem. Biophys. Res. Commun. 166(3), 1300–1307, Feb. 1990.

*Primary Examiner*—Evelyn Mei Huang
*Attorney, Agent, or Firm*—Burns, Doane, Swecker & Mathis, L.L.P.

[57] ABSTRACT

The present invention relates to the use of at least one ligand which is specific for RXR receptors, in the preparation of a pharmaceutical composition to be administered systemically and intended to increase the cellular proliferation and/or differentiation modulatory activity of a ligand for at least one receptor of the superfamily of steroidal/thyroidal receptors, other than a ligand which is specific for the RXR receptors, and which can heterodimerize with the RXRs, which is applied topically.

18 Claims, No Drawings

USE OF LIGANDS WHICH ARE SPECIFIC FOR RXR RECEPTORS

BACKGROUND OF THE INVENTION

Technical Field of the Invention

The invention relates to the use of at least one ligand which is specific for RXR receptors, in the preparation of a pharmaceutical composition to be administered systemically.

All-trans-retinoic acid is known to be a potent modulator (i.e. an inhibitor or, on the contrary, a stimulator, depending on the nature of the cells treated) of the differentiation and proliferation of many normal or transformed cell types. For example, it inhibits the differentiation of epithelial cells such as the keratinocytes of the epidermis. It also inhibits the proliferation of many transformed cells such as melanoma cells.

It is known that, generally speaking, all-trans-retinoic acid acts on the differentiation and proliferation of cells by interacting with nuclear receptors referred to as RARs (retinoic acid receptors) contained in the cell nucleus. Three identified subtypes of RAR receptors exist at the present time, referred to, respectively, as RAR-α, RAR-β and RAR-γ. These receptors, after binding of the ligand (i.e. retinoic acid), interact with the promoter region of genes regulated by retinoic acid at specific response elements. To bind to the response elements, the RARs heterodimerize with another type of receptor known by the name of RXRs. The natural ligand of the RXRs is 9-cis-retinoic acid. The RXRs are considered to be "master regulatory proteins" since they interact with other members of the superfamily of steroidal/thyroidal receptors to form heterodimers, such as with the RARs, such as the vitamin $D_3$ receptor (VDR), the triiodothyroxine receptor (TR) and the PPARs (peroxisome proliferator activated receptors). Furthermore, the RXRs can interact with specific response elements in the form of homodimers.

Many synthetic structural analogues of all-trans-retinoic acid or of 9-cis-retinoic acid, commonly termed "retinoids", have been described to date in the literature. Some of these molecules are capable of binding and specifically activating RARs or, on the contrary, RXRs. Furthermore, some analogues may bind and activate one particular subtype of RAR receptor (α, β or γ). Other analogues, lastly, do not display any particular selective activity with respect to these different receptors. In this connection, for example, 9-cis-retinoic acid activates both RARs and RXRs, without significant selectivity for one or other of these receptors (non-specific ligand), whereas all-trans-retinoic acid, for its part, selectively activates RARs (RAR-specific ligand), without discrimination between subtypes. Generally speaking and qualitatively, a given substance (or ligand) is termed specific with respect to a given family of receptors (or, respectively, with respect to a particular receptor of this family) when the said substance displays a strong affinity for all the receptors of this family (or, respectively, for the particular receptor of this family) and when it displays, moreover, a weak affinity for all the receptors of any other family (or, respectively, for all other receptors, of this same family or otherwise).

On account of the activities mentioned above, it is also well known that retinoic acid, vitamin D or analogues thereof are used for the topical treatment of various dermatological diseases or in the cosmetic field.

However, their use may lead to considerable side effects, such as teratogenicity and/or irritation for the ligands which are selective for the RAR receptors, and hypercalcaemia for vitamin D or analogues thereof. The ligands which are selective for the RXR receptors are themselves known to have little, or even no, teratogenic, irritant and/or hypercalcaemic activity.

The Applicant has just discovered, entirely surprisingly, that when a ligand for at least one receptor of the superfamily of steroidal/thyroidal receptors, other than a ligand which is specific for the RXR receptors, and one which can heterodimerize with the RXRs, is applied topically, its activity may be synergized by the systemic (other than topical: parenteral, enteral, including the oral route) administration of at least one ligand which is specific for the RXR receptors. This result is unexpected insofar as when it is used alone and at comparable doses, a ligand which is specific for RXRs has no or substantially no activity. It is all the more surprising to observe this synergy given that the two types of compound used are administered via different routes.

Thus, the subject of the present invention is the use of at least one ligand which is specific for RXR receptors, in the preparation of a pharmaceutical composition to be administered systemically and intended to increase the cellular proliferation and/or differentiation modulatory activity of a ligand for at least one receptor of the superfamily of steroidal/thyroidal receptors, other than a ligand which is specific for the RXR receptors, and which can heterodimerize with the RXRs, which is applied topically.

The present invention has the advantage of being able to decrease the topically administered doses of ligands for at least one receptor of the superfamily of steroidal/thyroidal receptors, other than a ligand which is specific for the RXR receptors, and which can heterodimerize with the RXRs, while at the same time having the same activity and thus the same efficacy, but while decreasing their side effects, in particular the teratogenic or hypercalcaemic effects of some of these ligands, such as the ligands which are specific for the RAR or VDR receptors respectively.

Other characteristics, aspects, subjects and advantages of the invention will emerge even more clearly on reading the description which follows, as well as the various concrete, but in no way limiting, examples intended to illustrate it.

The ligand for at least one receptor of the superfamily of steroidal/thyroidal receptors, other than a ligand which is specific for the RXR receptors, and which can heterodimerize with the RXRs, is preferably chosen from ligands for the RARs (retinoic acid receptors), for the VDR (vitamin D3 receptor), for the PPARs (peroxisome proliferator activated receptors) or for the TR (triiodothyroxine receptor). Even more preferably, this ligand is chosen from ligands for the RARs and ligands for the VDR.

Preferably, the ligand for at least one receptor of the superfamily of steroidal/thyroidal receptors, other than a ligand which is specific for the RXR receptors, and which can heterodimerize with the RXRs, is specific for one of these receptors. The specificity of this ligand is determined according to the methods indicated below.

The specific or non-specific nature of a given substance with respect to one or more given nuclear or cytosolic receptors may be determined by means of tests which are standard for those skilled in the art. These tests are described in particular in the following references: (1) "Selective Synthetic Ligands for Nuclear Retinoic Acid Receptor Subtypes" in Retinoids: Progress in Research and Clinical Applications, Chapter 19 (pp. 261–267), Marcel Dekker Inc., edited by Maria A. Livrea and Lester Packer; (2) "Synthetic Retinoids: Receptor Selectivity and Biological Activity" in Parmacol. Skin, Basle, Karger, 1993, Volume 5, pp. 117–127; (3) "Selective Synthetic Ligands for Human Nuclear Retinoic Acid Receptors" in Skin Pharmacology, 1992, Vol. 5, pp. 57–65; (4) "Identification of Synthetic Retinoids with Selectivity for Human Nuclear Retinoic Acid Receptor-γ" in Biochemical and Biophysical Research Communications, Vol. 186, No. 2, July 1992, pp. 977–983; (5) "Selective High Affinity RAR-α or RAR-β Retinoic Acid Receptor Ligands" in Mol. Pharmacol., Vol. 40, pp. 556–562. Quantitatively, it is generally accepted that any substance which, with regard to a given first receptor, has a dissociation constant (Kd) which is at least 10 times as low, and preferably at least 15 times as low, as the Kd which it has with respect to a given second receptor, may be qualified as a substance which is specific for this first receptor relative to this second receptor.

As examples of ligands which are specific for RARs and which can be used in the context of the present invention, mention may be made in particular of:

all-trans-retinoic acid, 2-(5,6,7,8-tetrahydro-5,5,8,8-tetramethyl-2-naphthyl)-6-benzo[b]thiophenecarboxylic acid, 4-[(5,6,7,8-tetrahydro-5,5,8,8-tetramethyl-2-naphthyl) carboxamido]benzoic acid, 4-[(5,6,7,8-tetrahydro-5,5,8,8-tetramethyl-2-naphthyl) carbamoyl]benzoic acid.

Examples of compounds which are specific for the VDR receptor and which may be mentioned are the following vitamin D derivatives:

1α,25-dihydroxyvitamin D3,

1α-hydroxyvitamin D3, 25-hydroxyvitamin D3,

1α,25-dihydroxyvitamin D2,

1α,24-dihydroxyvitamin D2.

Among the ligands which are specific for PPAR receptors and which may be mentioned in particular are bromopalmitic acid and analogues thereof.

Lastly, as examples of ligands which are specific for RXRs and which are suitable for use in the invention, mention may be made here more particularly of:

4-[(5,6,7,8-tetrahydro-5,5,8,8-tetramethyl-2-naphthyl) carbonylethyleneacetal]benzoic acid, (E)-2-[2-(3,5,5,8,8-pentamethyl-5,6,7,8-tetrahydro-2-naphthyl)-1-propenyl]-4-thiophenecarboxylic acid, 4-[(3,5,5,8,8-pentamethyl-5,6,7,8-tetrahydro-2-naphthyl) carbonyl]benzoic acid.

In the following and in the foregoing text, the term topical route is understood to refer to any technique of administration of a product by direct application of this product to a surface (or external) part of the body, such as the skin, the scalp, the nails or the mucous membranes, and the term systemic route is understood to refer to any technique of administration of a product by a route other than topical, for example the enteral and/or parenteral route. In the case of the systemic route, the oral route is preferably used.

Via the enteral route, and more particularly the oral route, the compositions containing the ligand or ligands which is/are specific for the RXRs may be in the form of tablets, gelatin capsules, coated tablets, syrups, suspensions, solutions, powders, granules, emulsions, microspheres or nanospheres or polymeric or lipid vesicles which allow controlled release. Via the parenteral route, these compositions may be in the form of solutions or suspensions for infusion or for injection.

The ligand or ligands which is/are specific for the RXRs in accordance with the invention are generally administered at daily doses of approximately from 0.01 mg/kg to 100 mg/kg of body weight, preferably of from 10 to 50 mg/kg, these doses being taken from 1 to 3 times/day.

Via the topical route, the compositions containing the ligand or ligands for at least one receptor of the superfamily of steroidal/thyroidal receptors, other than a ligand which is specific for the RXR receptors, and which can heterodimerize with the RXRs, and which are thus more particularly intended for the treatment of the skin or of the mucous membranes, may be in the form of ointments, creams, milks, salves, powders, impregnated pads, solutions, gels, sprays, lotions or suspensions. They may also be in the form of microspheres or nanospheres or polymeric or lipid vesicles or polymeric patches and hydrogels which allow controlled release of the active agents. These topical-route compositions may moreover be either in anhydrous form or in an aqueous form, depending on the clinical indication.

The compositions for topical use in accordance with the invention contain the ligand or ligands for at least one receptor of the superfamily of steroidal/thyroidal receptors, other than a ligand which is specific for the RXR receptors, and which can heterodimerize with the RXRs, at a concentration generally of between 0.001% and 10% by weight, preferably of between 0.01% and 1% by weight, relative to the total weight of the composition.

The compositions intended for topical use containing the ligand or ligands for at least one receptor of the superfamily of steroidal/thyroidal receptors, other than a ligand which is specific for the RXR receptors, and which can heterodimerize with the RXRS, or the compositions intended for systemic use containing the ligand or ligands which is/are specific for the RXRs, may, obviously, also contain inert or even pharmacodynamically active additives or combinations of these additives and, in particular: wetting agents; depigmenting agents such as hydroquinone, azelaic acid, caffeic acid or kojic acid; emollients; moisturizing agents such as glycerol, PEG 400, thiamorpholinone and derivatives thereof or alternatively urea; antiseborrhoeic or antiacne agents, such as S-carboxymethylcysteine, S-benzylcysteamine, salts thereof or derivatives thereof, or benzoyl peroxide; antifungal agents such as ketoconazole or poly(4,5-methylene-3-isothiazolidones); antibacterial agents, carotenoids and, in particular, β-carotene; antipsoriatic agents such as anthralin and derivatives thereof; and, lastly, eicosa-5,8,11,14-tetraynoic acid and eicosa-5,8, 11-triynoic acid, and esters and amides thereof.

The compositions according to the invention may also contain flavour enhancers, preserving agents such as parahydroxybenzoic acid esters, stabilizers, moisture regulating agents, pH regulating agents, osmotic-pressure modifying agents, emulsifiers, UV-A and UV-B screening agents, and antioxidants such as α-tocopherol, butylated hydroxylated anisole or butylated hydroxytoluene.

Obviously, a person skilled in the art will take care to choose the optional compound or compounds to be added to these compositions such that the advantageous properties intrinsically associated with the present invention are not, or are substantially not, altered by the addition envisaged.

The cellular proliferation and/or differentiation modulatory activity of the ligands for at least one receptor of the superfamily of steroidal/thyroidal receptors, other than a ligand which is specific for the RXR receptors, and which can heterodimerize with the RXRs, thus allows them to be used in the following fields of treatment:

(1) for treating dermatological complaints associated with a keratinization disorder which has a bearing on differentiation and on proliferation, in particular for treating common acne, comedones, polymorphonuclear leukocytes, acne rosacea, nodulocystic acne, acne conglobata, senile acne and secondary acnes such as solar, medication-related or professional acne, (2) for treating other types of keratinization disorder, in particular ichthyosis, ichthyosiform states, Darier's disease, palmoplantar keratoderma, leucoplasias and leucoplasiform states, and cutaneous or mucous (buccal) lichen, (3) for treating other dermatological complaints associated with a keratinization disorder with an inflammatory and/or immunoallergic component and, in particular, all forms of psoriasis, whether it be cutaneous, mucous or ungual, and even psoriatic rheumatism, or alternatively cutaneous atopy, such as eczema or respiratory atopy or alternatively gingival hypertrophy; the compounds may also be used in certain inflammatory complaints which do not display any keratinization disorder, (4) for treating all dermal or epidermal proliferations, whether benign or malignant and whether they be of viral origin or otherwise, such as common warts, flat warts and verruciform epidermodysplasia, it being also possible for the oral or florid papillomatoses and the proliferations to be induced by ultraviolet radiation, in particular in the case of basocellular and spinocellular epithelioma, (5) for treating other dermatological disorders such as bullosis and collagen diseases, (6) for treating certain ophthalmological disorders, especially corneopathies, (7) for repairing or combating ageing of the skin, whether it be photo-induced or chronological ageing, or for reducing actinic keratoses and pigmentations, or any pathologies associated with chronological or actinic ageing, (8) for preventing or curing the stigmata of epidermal and/or dermal atrophy induced by local or systemic corticosteroids, or any other form of cutaneous atrophy, (9) for preventing or treating cicatrization disorders or for preventing or repairing vibices, or alternatively for improving cicatrization,

(10) for combating disorders of sebaceous functioning such as the hyperseborrhoea of acne or simple seborrhoea,

(11) in the treatment or prevention of cancerous or precancerous states,

(12) in the treatment of inflammatory complaints such as arthritis,

(13) in the treatment of any skin or general complaint of viral origin,

(14) in the prevention or treatment of alopecia,

(15) in the treatment of dermatological or general complaints having an immunological component,

(16) in the treatment of complaints of the cardiovascular system such as arteriosclerosis,

(17) in the treatment or prevention of cellulitis, obesity or diabetes,

(18) in the treatment of mycoses, such as onychomycosis.

The ligands for at least one receptor of the superfamily of steroidal/thyroidal receptors, other than a ligand which is specific for the RXR receptors, and which can heterodimerize with the RXRs, also find an application in the cosmetic field, in particular in body and hair hygiene and in particular for the treatment of skin types with a tendency towards acne, for the regrowth of hair, for preventing hair loss, for combating the greasy appearance of the skin or the hair, in the protection against the harmful effects of the sun or in the treatment of physiologically dry skin types, and for preventing and/or combating photoinduced or chronological ageing.

Thus, another subject of the present invention is a cosmetic process for increasing the cellular proliferation and/or differentiation modulatory activity of a ligand for at least one receptor of the superfamily of steroidal/thyroidal receptors, other than a ligand which is specific for the RXR receptors, and which can heterodimerize with the RXRs, which is applied topically, characterized in that at least one ligand which is specific for the RXR receptors is used, via the systemic route.

In the cosmetic field, as in the pharmaceutical field, the ligands for at least one receptor of the superfamily of steroidal/thyroidal receptors, other than a ligand which is specific for the RXR receptors, and which can heterodimerize with the RXRs, or the ligands which are specific for the RXRs, can be employed in combination with other retinoids, with other D vitamins or derivatives thereof, with corticosteroids, or alternatively in combination with anti-free-radical agents, with hydroxy acids or keto acids or derivatives thereof, or alternatively with ion-channel blockers.

Several examples intended, on the one hand, to demonstrate the effects associated with the present invention, and, on the other hand, to illustrate various concrete formulations in accordance with the invention, will now be given, without any limitation being implied.

EXAMPLE 1

The aim of this example is to demonstrate the synergistic effect afforded by a given ligand which is specific for RXRs, via the oral route in vivo, on the activity of a ligand which is specific for RARs applied topically to mouse ear.

It has indeed been shown that retinoic acid, which is used for the topical treatment of various dermatological diseases, in single topical administration to mouse ear induces a proliferation of the epidermis (Arch. Dermatol, Res. 1992, 284:418–423), erythema and oedema of this ear, these responses being dependent on the dose administered. These clinical signs are also conventionally observed during the topical application of retinoic acid in man.

Furthermore, it has been shown that these effects can be inhibited specifically by an RAR receptor antagonist, which is thereby in support of a mechanistic connection between the interaction of the ligand with its receptors and the clinical effects induced.

The test used to evaluate this synergistic effect is thus that of oedema of mouse ear induced by topical application of 2-(5,6,7,8-tetrahydro-5,5,8,8-tetramethyl-2-naphthyl)-6-benzo[b]thiophenecarboxylic acid (retinoic acid analogue) at a concentration of 0.003% on a weight-for-volume basis. According to this model, a topical application of 2-(5,6,7,8-tetrahydro-5,5,8,8-tetramethyl-2-naphthyl)-6-benzo[b]thiophenecarboxylic acid to the ear causes an inflammation which is characterized by an increase in the thickness of the ear, this thickness reaching a maximum 5 days after the application. This response can thus be quantified by measuring the thickness of the ear by an oditest.

The exact procedure is as follows: 10 mice are first treated with 2-(5,6,7,8-tetrahydro-5,5,8,8-tetramethyl-2-naphthyl)-6-benzo[b]thiophenecarboxylic acid (compound A), making a topical application onto one of their ears, at time t=0, with 20 μl of an acetone solution comprising 0.003% on a weight-for-volume basis of 2-(5,6,7,8-tetrahydro-5,5,8,8-tetramethyl-2-naphthyl)-6-benzo[b]thiophenecarboxylic acid. 4-[(3,5,5,8,8-Pentamethyl-5,6,7,8-tetrahydro-2-naphthyl)carbonyl]benzoic acid (compound B) in oil of cremophor type (EL 25%) is given orally to 5 (=group 2) out of the 10 mice thus treated, from t=0 and once a day for 11 days. The 5 mice which have not received compound B constitute group 1. The oedematous response is quantified by measuring the thickness of the ear at t=5 or 6 days. The results are then expressed as a % of the synergistic effect calculated in the following way:

Mouse ear thickness (Group 2)–Mouse ear thickness (Group 1)×100

Mouse ear thickness (Group 1)

The results obtained are collated in the following Table 1.

TABLE 1

| Topical route | Dose (% W/V) | Oral route | Dose (mg/kg) | Synergistic effect (%) |
|---|---|---|---|---|
| Compound A | 0.003 | Compound B | 0 | 0 |
| Compound A | 0.003 | Compound B | 10 | 73 |
| Compound A | 0.003 | Compound B | 30 | 118 |

W/V indicates a weight-for-volume basis.

Furthermore, the analogous application of a ligand which is specific for the RXRs alone, such as compound B, via the oral route induces no response in the mouse.

Thus, it is clearly demonstrated by means of this test that the combination of a ligand for at least one receptor of the superfamily of steroidal/thyroidal receptors, other than a ligand which is specific for the RXR receptors, and which can heterodimerize with the RXRs, with a ligand which is specific for the RXRs considerably increases the response of mouse ear when compared with the response induced by sole topical application of a ligand for at least one receptor of the superfamily of steroidal/thyroidal receptors, other than a ligand which is specific for the RXR receptors, and which can heterodimerize with the RXRs.

EXAMPLE 2

Various concrete formulations are illustrated in this example (compounds A and B are those defined above in Example 1). The formulations comprising compound A are intended for topical administration and the formulations comprising compound B are intended for oral administration, it being necessary for both formulations to be taken in combination during a treatment. Thus, the formulations comprising compound B can be administered orally before, during or after topical application of the formulations comprising compound A.

A- ORAL ROUTE:

(a) 0.2 g tablet
| | |
|---|---|
| Compound B | 0.002 g |
| Starch | 0.113 g |
| Dicalcium phosphate | 0.020 g |
| Silica | 0.020 g |
| Lactose | 0.030 g |
| Talc | 0.010 g |
| Magnesium stearate | 0.005 g |

(b) Drinkable suspension in 10 ml ampules
| | |
|---|---|
| Compound B | 0.1 g |
| Glycerol | 1.000 g |
| 70% sorbitol | 1.000 g |
| Sodium saccharinate | 0.010 g |
| Methyl para-hydroxybenzoate | 0.080 g |
| Flavoring qs | |
| Purified water qs | 10 ml |

B - TOPICAL ROUTE:

(a) Ointment
| | |
|---|---|
| Compound A | 0.2 g |
| Isopropyl myristate | 81.520 g |
| Liquid petrolatum oil | 9.100 g |
| Silica ("Aerosil 200" sold by Degussa) | 9.180 g |

(b) Nonionic water-in-oil cream
| | |
|---|---|
| Compound A | 0.100 g |
| Mixture of emulsifying lanolin alcohols, waxes and oils ("anhydrous Eucerin" sold by BDF) | 39.900 g |
| Methyl para-hydroxybenzoate | 0.075 g |
| Propyl para-hydroxybenzoate | 0.075 g |
| Sterile demineralized water qs | 100 g |

(c) Lotion
| | |
|---|---|
| Compound A | 0.200 g |
| Polyethylene glycol (PEG 400) | 69.800 g |
| 95% ethanol | 30.000 g |

(d) Hydrophobic ointment
| | |
|---|---|
| Compound A | 0.600 g |
| Isopropyl myristate | 36.400 g |
| Silicone Oil ("Rhodorsil 47 V 300" sold by Rhône-Poulenc) | 36.400 g |
| Beeswax | 13.600 g |
| Silicone oil ("Abil 300,000 cst" sold by Goldschmidt) qs | 100 g |

(e) Nonionic oil-in-water cream
| | |
|---|---|
| Compound A | 1.000 g |
| Cetyl alcohol | 4.000 g |
| Glyceryl monostearate | 2.500 g |
| PEG 50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water qs | 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for treating inflammation in a mammal comprising topically administering a ligand specific for a VDR receptor or an RAR receptor and systemically administering a ligand specific to a RXR receptor in relative amounts effective to treat inflammation to a mammal in need thereof.

2. The method according to claim 1, wherein said ligand specific for the VDR receptor is selected from the group consisting of 1α,25-dihydroxyvitamin D3; 1α-hydroxyvitamin D3; 25-hydroxyvitamin D3; 1α,25-dihydroxyvitamin D2; and 1α,24-dihydroxyvitamin D2.

3. The method according to claim 1, wherein said ligand specific for at least one RXR receptor is administered orally.

4. The method according to claim 1, wherein the ligand which is specific for at least one RXR receptor is administered daily at a dosage ranging from about 0.01 to 100 mg/kg of body weight.

5. The method according to claim 1, wherein said VDR or RAR receptor ligand is administered at a concentration ranging from about 0.001% to 10% by weight.

6. The method according to claim 5, wherein said dosage ranges from 0.01 to 1% by weight relative to the total weight of the composition.

7. The method according to claim 1, wherein said ligand specific for RXR receptors is selected from the group consisting of 4-[(5,6,7,8-tetrahydro-5,5,8,8-tetramethyl-2-naphthyl)carbonylethyleneacetal]benzoic acid; (E)-2-[2-(3,5,5,8,8-pentamethyl-5,6,7,8-tetrahydro-2-naphthyl)-1-propenyl]-4-thiophenecarboxylic acid; and 4-[(3,5,5,8,8-pentamethyl-5,6,7,8-tetrahydro-2-naphthyl)carbonyl] benzoic acid.

8. The method according to claim 7, wherein said ligand specific for RARs is selected from the group consisting of all-trans-retinoic acid; 2-(5,6,7,8-tetrahydro-5,5,8,8-tetrarnethyl-2-naphthyl)-6-benzor[b]thiophenecarboxylic acid; 4-[(5,6,7,8-tetrahydro-5,5,8,8-tetramethyl-2-naphthyl) carboxamido]benzoic acid; and 4[(5,6,7,8-tetrahydro-5,5,8,8-tetramethyl-2-naphthyl)carbamoyl]benzoic acid.

9. The method according to claim 7, wherein said ligand specific for the VDR receptor is selected from the group consisting of 1α,25-dihydroxyvitamin D3; 1α-hydroxyvitamin D3; 25-hydroxyvitamin D3; 1α,25-dihydroxyvitamin D2; and 1α,24-dihydroxyvitamin D2.

10. The method of claim 1, wherein said ligand specific for VDR is calcitriol or calcipotriol.

11. The method of claim 1, wherein the ligand specific for RXR is 6-(3,5,5,8,8-pentamethyl-5,6,7,8-tetrahydro-naphthalene-2-ylsulfanyl) nicotinic acid.

12. The method of claim 1, wherein systemic administration is selected from the group consisting of enteral or parenteral administration.

13. The method of claim 12, wherein enteral administration is effected using a dosage formulation selected from the group consisting of tablets, gelatin capsules, coated tablets, syrups, suspensions, solutions, powders, granules, emulsions, microspheres, nanospheres, polymeric vesicles, and lipid vesicles comprising said ligand specific to an RXR receptor.

14. The method of claim 12, wherein parenteral administration is effected using a solution or suspension comprising said ligand specific for an RXR ligand.

15. The method of claim 1, wherein topical administration of said ligand specific for an RAR or VDR receptor is effected using a formulation selected from the group consisting of an ointment, cream, salve, powder, impregnated pad, solution, gel, spray, lotion and suspension comprising said ligand.

16. The method of claim 15, wherein said formulation is in anhydrous or aqueous form.

17. The method of claim 15, wherein said formulation further comprises at least one inert or pharmaceutically active additive selected from the group consisting of wetting agents, depigmentaing agents, emollients, moisturizing agents, antiseborrhoiec or antiacne agents, antifungal agents, antibacterial agents, carotenoids, anti-psoriatic agents, eicosa-5, 8, 11, 14-tetraynoic acid and eicosa-5, 8, 11-triynoic acid, ester and amides thereof.

18. The method of claim 17, wherein the depigmentaing agent is hydroquinone, azelaic acid, caffeic acid or kojic acid; the moisturizing agent is glycerol, PEG 400, thiamorpholinone or derivatives thereof, or urea; the antiseborrhoeic or antiacne agent is S-carboxymethylcysteine, S-benzylcysteamine, salts thereof or derivatives thereof, or benzoyl peroxide; the antifungal agent is ketoconazole or poly(4,5-methylene-3-isothiazolidones); the carotenoid is β-carotene; the anti-psoriatic agent is anthralin or derivatives thereof.

* * * * *